US00RE44733E

(19) United States
(12) Reissued Patent
Zhang et al.

(10) Patent Number: US RE44,733 E
(45) **Date of Reissued Patent: *Jan. 28, 2014**

(54) 6-MERCAPTO-CYCLODEXTRIN DERIVATIVES:REVERSAL AGENTS FOR DRUG-INDUCED NEUROMUSCULAR BLOCK

(75) Inventors: Mingiang Zhang, Montreal (CA); Ronald Palin, Banton (GB); Jonathan Bennett, Edinburgh (GB)

(73) Assignee: Merck Sharp & Dohme B.V., Haarlem (NL)

( * ) Notice: This patent is subject to a terminal disclaimer.

(21) Appl. No.: 13/432,742

(22) Filed: Mar. 28, 2012

Related U.S. Patent Documents

Reissue of:
(64) Patent No.: 6,670,340
Issued: Dec. 30, 2003
Appl. No.: 10/148,307
PCT Filed: Nov. 23, 2000
PCT No.: PCT/EP00/11789
§ 371 (c)(1),
(2), (4) Date: Aug. 19, 2002
PCT Pub. No.: WO01/40316
PCT Pub. Date: Jun. 7, 2001

U.S. Applications:
(63) Continuation of application No. 10/148,307.

(30) Foreign Application Priority Data

Nov. 29, 1999 (EP) ..... 99309558

(51) Int. Cl.
*A61K 31/724* (2006.01)
*A61K 31/715* (2006.01)
*A61K 31/537* (2006.01)
*A61K 31/452* (2006.01)
*A61K 31/225* (2006.01)
*A61P 25/00* (2006.01)
*C08B 37/16* (2006.01)

(52) U.S. Cl.
USPC ..... 514/58; 514/231.5; 514/316; 514/547; 536/103

(58) Field of Classification Search
None
See application file for complete search history.

(56) References Cited

U.S. PATENT DOCUMENTS

| | | | | |
|---|---|---|---|---|
| 3,929,813 | A | | 12/1975 | Higuchi et al. |
| 4,599,327 | A | | 7/1986 | Nogradi |
| 4,603,123 | A | | 7/1986 | Chiesi |
| 4,727,064 | A | | 2/1988 | Pitha |
| 4,816,462 | A | | 3/1989 | Nowicky |
| 4,834,985 | A | | 5/1989 | Elger |
| 4,869,904 | A | | 9/1989 | Uekama |
| 4,983,586 | A | | 1/1991 | Bodor |
| 4,983,636 | A | | 1/1991 | Takeuchi |
| 5,002,935 | A | | 3/1991 | Bodor |
| 5,008,386 | A | | 4/1991 | Szabo |
| 5,017,566 | A | | 5/1991 | Bodor |
| 5,180,716 | A | | 1/1993 | Yaksh et al. |
| 5,250,520 | A | * | 10/1993 | Kurita et al. ..... 514/58 |
| 5,385,891 | A | | 1/1995 | Moriya et al. |
| 5,767,112 | A | | 6/1998 | Poll et al. |
| 5,834,446 | A | * | 11/1998 | Dow et al. ..... 514/58 |
| 5,840,881 | A | | 11/1998 | Uda et al. |
| 5,935,941 | A | | 8/1999 | Pitha |
| 6,670,340 | B1 | | 12/2003 | Akzo |
| 6,949,527 | B2 | | 9/2005 | Akzo |
| 7,026,304 | B2 | | 4/2006 | Zhang et al. |
| 7,265,099 | B1 | | 9/2007 | Organon |
| 2002/0111377 | A1 | | 8/2002 | Stinchcomb |
| 2002/0173550 | A1 | | 11/2002 | Calignano |
| 2004/0029833 | A1 | | 2/2004 | Zhang |

FOREIGN PATENT DOCUMENTS

| | | | |
|---|---|---|---|
| AU | 36628 95 | | 9/1996 |
| EP | 0197571 | | 4/1986 |
| EP | 0 447 171 | A | 9/1991 |
| EP | 0447 171 | B1 | 2/1994 |
| EP | 0465535 | | 3/1998 |
| JP | 11-246603 | | 9/1999 |
| WO | WO9200331 | | 1/1992 |
| WO | WO 97/17977 | * | 5/1997 |

(Continued)

OTHER PUBLICATIONS

Baer, H. et al "Heptakis[6-S-(2,3-dihydroxypropyl)-6-thio]cyclomaltoheptaose . . ." Carbohyd. Res. (1996) vol. 280, pp. 315-321.*

(Continued)

*Primary Examiner* — Leigh Maier
(74) *Attorney, Agent, or Firm* — Keith D. MacMillan; Gerard M. Devlin

(57) ABSTRACT

Disclosed is a 6-mercapto-cyclodextrin derivative having general formula (I) wherein m is 0-7 and n is 1-8 and m+n=7 or 8; R is $(C_{1-6})$alkylene, optionally substituted with 1-3 OH groups, or $(CH_2)_o$-phenylene-$(CH_2)_p$—; o and p are independently 0-4; X is COOH, $CONHR_1$, $NHCOR_2$, $SO_2OH$, $PO(OH)_2$, $O(CH_2—CH_2—O)_q$—H, OH or tetrazol-5-yl; $R_1$ is H or $(C_{1-3})$alkyl; $R_2$ is carboxyphenyl; q is 1-3; or pharmaceutically acceptable salts thereof. The 6-mercaptocyclodextrin derivative is highly suitable for use in the reversal of drug-induced neuromuscular block.

(I)

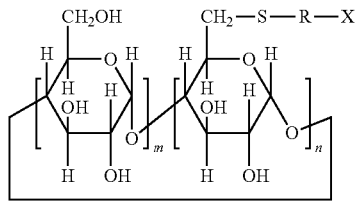

21 Claims, No Drawings

(56) References Cited

FOREIGN PATENT DOCUMENTS

| | | | |
|---|---|---|---|
| WO | WO01/12202 | A2 | 2/2001 |
| WO | WO01/40316 | A1 | 7/2001 |
| WO | WO 2004000832 | A | 12/2003 |

OTHER PUBLICATIONS

Guillo, F. et al "Synthesis of symmetrical cyclodextrin derivatives . . ." Bull. Soc. Chim. Fr. (1995) vol. 132, pp. 857-866.*
Supplementary European Search Report dated Jul. 20, 2001, for related International Application No. PCT/EP00/076494.
Kuroda, et al; J. Chem. Soc. Perkin Trans, 1989; "Dynamic Molecular Motions of p-Methylcinnamic Acid included in B-Cyclodextrin Derivatives: A New Type of Free-energy Relationship in Complex Formation", pp. 1409-1416.
Hamelin, B., et al., American Chemical Society; 1995; "Formation of Highly Stable Heterodimers in Aquaeous Solution between B-Cyclodextrin Derivatives Bearing Multiple Opposite Charges"; 99, pp. 17877-17885.
Adam, J. M., et. al; J. Med. Chem; Cyclodextrin-Derived Host Moleculaes as Reversal agents for the Neuromuscular Blocker Rocuronium Bromide: Synthesis and Structure—Activity Relationships, (2002), vol. 45, pp. 1806-1816.
AshtonP.R., et al., Chem. Eur. J., Synthetic Cyclic Oligosaccharides-Syntheses and Structural Properties of a Cyclo(1-4) . . . , (1986), vol. 2, No. 5, pp. 580-591.
Zhang, M.G, Drug-specific cyclodextrins: the future of rapid neuromuscular block reversal?: Drugs of the Future (2003), vol. 28, No. 4, pp. 347-354.
Richardson, JD; "Cannabinoids modulate pain by multiple mechanism of action", Journal of Pain 2000, vol. 1; No. 1; 2000; pp. 2-14.
Tarver, G. J. et al., 2-O-Substituted Cyclodextrins as Reversal Agents for the Neuromuscular Blocker Rocuronium Bromide, Bioorganic & Medicinal Chemistry (2002) vol. 10, pp. 1819-1827.
Lindberg, et. al., Carbohydrate Research,"Synthesis of some 2-0-(2-hydroxyalkyl) and 2-0-(2,3-di-hydroxyalkyl) derivatives of cyctomaltoheptaose", 22, 1991, pp. 113-119.
Bom, A, et. al. , Angew Chem Int Ed; "A Novel Concept of Reversing Neuromuscular Block: Chemical Encapsulation of Rocuronium Bromide by a Cyclodextrin-Based Synthetic Host", (2002), vol. 41, No. 2,pp. 266-270.
Desire, B, et. al., Experientia; "Inactivation of sarin and soman by cyclodextrins in vitro", vol. 43, No. 4, (1987), pp. 395-397.
Desire, B. et al. "Interaction of Soman with □-Cyclodextrin1," Fundamental and Applied Toxicology, vol. 7, No. 4 (1986) pp. 646-657.
Stella, V. J. et al. "Cyclodextrins: Their Future in Drug Formulation and Delivery," Pharmaceutical Research, vol. 14, No. 5 (1997), pp. 556-567.
Khan, A. R. et al. "Methods for Selective Modifications of Cyclodextrins," Chem. Rev. (1998) vol. 98, pp. 1977-1996.
Szente, L. et al. "Highly soluble cyclodextrin derivatives: chemistry, properties, and trends in development," Advanced Drug Delivery Reviews (1999) vol. 36, pp. 17-28.
Gattuso, G. et al. "Synthetic Cyclic Oligosaccharides," Chem. Rev. (1998) vol. 98, pp. 1919-1958.
Vogtle, et al. Comprehensive Supramolecular Chemistry, vol. 2, Molecular recognition: Receptors for molecular guests, Atwood et al. eds; Elsevier Science Ltd., Oxford, UK (1996) pp. 211-266.
Miyake, M. et al. "Anionic Cyclophanes as Hosts for Cationic Aromatic Guests," Tetrahedron Letters, vol. 32, No. 49 (1991) pp. 7295-7298.
Soga, T. et al. Modifications of Hydrophobic Cavity and their Effects on the Complex Formation with a Hydrophobic Substrate, Tetrahedron Letters, vol. 21 (1980) pp. 4351-4354.
May, C. et al. "Development of a toxin-binding agent as a treatment for tunicaminyluracil toxicity: protection against tunicamycin poisoning of sheep," Australian Veterinary Journal, vol. 76, No. 11 (1998) pp. 752-756.
Irie, T. et al. "Protective mechanism of □-cyclodextrin for the hemolysis induced with phenothiazine neuroleptics in vitro," J. Pharm. Dyn., vol. 6, No. 6 (1983) pp. 408-414.
Uekama, K., et al., Effects of cyclodextrins on chlorpromazine-induced haemolysis and central nervous system responses:, J. Pharm. Pharmacol, vol. 33, No. 11 (1981), pp. 707-710.
Alvarez-Gomes, J.A., et al., "Reversal of vecuronium-induced shallow neuromuscular blockade is significantly faster with sugammadex compared with neostigmine", Eur. J. Anasthesiol, 2007; 24(Suppl 39); Abstract 9AP7-8.
Anderson, W.R., et al., "Brain-enhanced delivery of testosterone using a chemical delivery system complexed with 2-hydroxypropyl-b-cyclodextrin", 1997, Drug Design and Delivery, 2; 287-298.
Baer, et al., Carbohydrate Research, 280 (1996); Keptakis[6-S-(2,3-dihydroxypropyl)-6-thio] cyclomaltoheptaose and its sulfone: water-soluble B-cyclodextrin derivatives having modified polarity, pp. 315-321.
Bisson, AP, et al., Che. Eur. J., "Cooperative Ineractions in a Ternary Mixture", (1998), vol. 4, No. 5, pp. 845-851.
Connors, K.A., Wiley Interscience, "Binding Constants. The measurement of molecular complex stability" (1987), New York, pp. 24-28.
Cram, D.J., et al., Am Chem Soc., "Macro Rings VIII. Aromatic Substitution of the (6,6) Paracyclophane", 1955, vol. 77, pp. 1179-1186.
Gennaro, A. R., et al., "Parental Preparations" Chapter 84, Remington's Pharmaceutical Sciences, 18$^{th}$ Ed. Mack Publishing Company (1990) pp. 1570-1580.
Gennaro, A. R., et al., "Intravenous Admixtures" Chapter 85, Remington's Pharmaceutical Sciences, 18$^{th}$ Ed. Mack Publishing Company (1990) pp. 1545-1569.
Golden, J. H. "*Bi*(*anthracene*-9,10-*dimethylene*) (*Tetrabenzo*-[2,2]-*para-cyclophane*].," J. Chem. Soc. (1961) pp. 3741-3748.
Guillo, et al., Bull. Chim. Soc. Fr., vol. 132, "Synthesis of Symmetrical cyclodextrin derivatives bearing multiple charges"; Jul. 4, 1995; pp. 857-866.
Jicsinszky, L., et al., Comprehemsive Supramolecular Chemistry, vol. 3, Cyclodextrins, Elsevier Science Ltd., Oxford UK (1996) pp. 57-188.
Jones, RK, et al., "Reversal of Profound Rocuronium-induced Blockade with Sugammadex: A Rando . . .", Anesthesiology 2008: 109; 816-24.
Lee, C., et al., "Reversal of Profound Neuromuscular Block by Sugammadex Administered Three Minutes After Rocuronium", Anesthesiology, V. 110, No. 5, May 2009.
Loukas, Y. L., "Measurement of Molecular Association in Drug: Cyclodextrin Inclusion Complexes with Improved $^1$H NMR Studies," J. Pharm. Pharmacol (1997) vol. 49, pp. 944-948.
Miyake, M. et al. "Biomimetic Studies Using Artificial Systems. VI.[1)] Design and Synthesis of Novel Cyclophanes Having Eight Carboxyl Groups on the Aromatic Rings[2)]," Chem. Pharm. Bull., vol. 41(7) (1993) pp. 1211-1213.
PCT Search Report and Written Opinion for International Application No. PCT/EP00/11789 (WO2001/40316, corresponding to US6670340) dated Nov. 2, 2002; 4 pages.
Pitha, et al., Int'l Journal of Pharmaceutics, "Hydroxypropyl-B-Cyclodextrin: preparation and Characterization; effects on Solubility of Drugs", vol. 29, Issue 1, pp. 73-82 (1986).
Pitha, et al., Life Sciences, "Drug Solubilizers to Aid Pharmacologists: Amorphous Cyclodextrin Derivatives", 43: 492-502 (1988).
Uekama, K., et al., "Cyclodextrin Drug Carrier Systems", Chem Rev. (1998) vol. 98. pp. 2045-2076.
Yaksh, T.L., et al., "Studies of pharmacology and pathology intrathecally administered 4-anilinopiperidine analogues and morphine in rat and cat," Anesthesiology, 64; 54-66. (1986).
Escandar, G.M., Spectrofluorometric determination of piroxicam in the presence and absence of beta-cyclodextrin, vol. 124, No. 4, Feb. 1999, pp. 587-597: abstract medline.
Fielding, L., Determination of association constants (Ka) from Solution NMR Data, Tetrahedron 56 (2000) 6151-6170, May 2000.
Hamelin, et al., Formation of highly stable heterodimers in aqueous solution between B-cyclodextrin derivatives bearing opposite charges, J. Phys. Chem., vol. 99, No. 51, Aug. 1995.

(56) References Cited

OTHER PUBLICATIONS

Kwak, et al, Determination of the binding of B-cyclodextrin derivatives to adamantine carboxylic acids using capillary electrophoresis, Chromatographia, vol. 43, No. 11/12, Dec. 1996.
Lee, et al., Structure, Confirmation, and action of neuromuscular blocking drugs, British Journal of Anaesthesia, 87 (5): 755-69 (2001).
Luna et al., Isolation and characterization by NMR spectroscopy of three monosubstituted 4-sulfobutyl ether derivatives of cyclmaltoheptaose (B-cyclodrextrin), Carbohydrate Research 299 (1997), 111-118.
Miller et al., Sugammadex: An opportunity to change the practice of anesthesiology?, International Anesthesia Research Society, vol. 104, No. 3, Mar. 2007.
Tubashi, I, et al., Artificial Receptors for Amino Acids in Water. Local Environmental Effect on Polar Recognition by 6A,6B-dideoxy-6A,6B-bis(carboxymethylthiol)-B-Cyclodextrin, J. Am. Chem. Soc. 108, 4514-4518, 1986).
Wenz, et al., "Synthesis of highly water-soluble cyclodextrin sulfonates by addition of hydrogen sulfite to cyclodextrin allyl ethers", Carbohydrate Research 322 (1999) 153-165.
Zarzycki, P.K., et al., The equilibrium constant of beta cyclodextrin-phenolphthalein complex: influence of temperature and tetrahydrofuran addition, vol. 18, No. 1-2, 1998, pp. 165-170.
Selected prosecution history of U.S. Appl. No. 10/603,355 (US6,949,527), including obviousness type double patenting rejection mailed Feb. 8, 2005 and applicant's response filed Mar. 9, 2005.
Selected prosecution history of U.S. Appl. No. 10/049,393 (US7265099), including obviousness type double patenting rejection mailed Dec. 31, 2003, and applicant's response; and obviousness-type double patenting rejection mailed Aug. 7, 2006 and Applicant's response.

* cited by examiner

6-MERCAPTO-CYCLODEXTRIN DERIVATIVES:REVERSAL AGENTS FOR DRUG-INDUCED NEUROMUSCULAR BLOCK

Matter enclosed in heavy brackets [ ] appears in the original patent but forms no part of this reissue specification; matter printed in italics indicates the additions made by reissue.

This is a National Stage filing under 35 USC 371 of PCT/EP00/11789, filed Nov. 23, 2000.

The invention relates to 6-mercapto-cyclodextrin derivatives, to their use for the preparation of a medicament for the reversal of drug-induced neuromuscular block, and to a kit for providing neuromuscular block and its reversal.

A neuromuscular blocking agent (NMBA, also called a muscle relaxant) is routinely used during the administration of anaesthesia to facilitate endotracheal intubation and to allow surgical access to body cavities, in particular the abdomen and thorax, without hindrance from voluntary or reflex muscle movement. NMBAs are also used in the care of critically-ill patients undergoing intensive therapy, to facilitate compliance with mechanical ventilation when sedation and analgesia alone have proved inadequate, and to prevent the violent muscle movements that are associated with electroconvulsive therapy treatment.

Based on their mechanisms of action, NMBAs are divided into two categories: depolarizing and non-depolarizing. Depolarizing neuromuscular blocking agents bind to nicotinic acetylcholine receptors (nAChRs) at the neuromuscular junction in a way similar to that of the endogenous neurotransmitter acetylcholine. They stimulate an initial opening of the ion channel, producing contractions known as fasciculations. However, since these drugs are broken down only relatively slowly by cholinesterase enzymes, compared to the very rapid hydrolysis of acetyl-choline by acetylcholinesterases, they bind for a much longer period than acetylcholine, causing persistent depolarization of the end-plate and hence a neuromuscular block. Succinylcholine (suxamethonium) is the best known example of a depolarizing NMBA.

Non-depolarizing neuromuscular blocking agents compete with acetylcholine for binding to muscle nAChRs, but unlike depolarizing NMBAs, they do not activate the channel. They block the activation of the channel by acetylcholine and hence prevent cell membrane depolarization, and as a result, the muscle will become flaccid. Most of the clinically-used NMBAs belong to the non-depolarizing category. These include tubocurarine, atracurium, (cis) atracurium, mivacurium, pancuronium, vecuronium, rocuronium and rapacuronium (Org 9487).

At the end of surgery or a period of intensive care, a reversal agent of NMBAs is often given to the patient to assist the recovery of muscle function. Most commonly used reversal agents are inhibitors of acetylcholinesterase (AChE), such as neostigmine, edrophonium and pyridostigmine. Because the mechanism of action of these drugs is to increase the level of acetylcholine at the neuromuscular junction by inhibiting the breakdown of acetylcholine, they are not suitable for reversal of depolarizing NMBAs such as succinylcholine. The use of AChE inhibitors as reversal agents leads to problems with selectivity, since neurotransmission to all synapses (both somatic and autonomic) involving the neurotransmitter acetylcholine is potentiated by these agents. This non-selectivity may lead to many side-effects due to the non-selective activation of muscarinic and nicotinic acetylcholine receptors, including bradycardia, hypotension, increased salivation, nausea, vomiting, abdominal cramps, diarrhoea and bronchoconstriction. Therefore in practice, these agents can be used only after or together with the administration of atropine (or glycopyrrolate) to antagonize the muscarinic effects of acetylcholine at the muscarinic receptors in the autonomic parasympathetic neuro-effector junctions (e.g. the heart). The use of a muscarinic acetylcholine receptor (mAChR) antagonist such as atropine causes a number of side-effects, e.g., tachycardia, dry mouth, blurred vision, difficulties in emptying the bladder and furthermore may affect cardiac conduction.

A further problem with anticholinesterase agents is that residual neuro-muscular activity must be present (>10% twitch activity) to allow the rapid recovery of neuromuscular function. Occasionally, either due to hyper-sensitivity of the patient or accidental overdose, administration of NMBAs can cause complete and prolonged block of neuromuscular function ("profound block"). At present, there is no reliable treatment to reverse such a 'profound block'. Attempts to overcome a 'profound block' with high doses of AChE inhibitors has the risk of inducing a "cholinergic crisis", resulting in a broad range of symptoms related to enhanced stimulation of nicotinic and muscarinic receptors.

In European Patent Application 99,306,411 (AKZO NOBEL N.V.) the use of chemical chelators (or sequestrants) as reversal agents has been disclosed. Chemical chelators capable of forming a guest-host complex for the manufacture of a medicament for the reversal of drug-induced neuromuscular block were described. The use of chemical chelators as reversal agents for NMBAs has the advantage that they are effective in reversing the action of both depolarizing and non-depolarizing NMBAs. Their use does not increase the level of acetylcholine and therefore they produce fewer side effects and none associated with the stimulation of muscarinic and nicotinic receptors seen with the AChE reversal agents. In addition, there is no need for the combined use of an AChE inhibitor and a mAChR antagonist (e.g., atropine), while the chemical chelators may further be safely employed for the reversal of 'profound block'. Examples of such chemical chelators, as disclosed in EP 99,306,411, were selected from various classes of, mostly cyclic, organic compounds which are known for their ability to form inclusion complexes with various organic compounds in aqueous solution, e.g. cyclic oligosaccharides, cyclophanes, cyclic peptides, calixarenes, crown ethers and aza crown ethers.

The cyclodextrins,

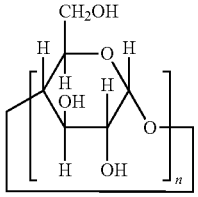

$n = 6\text{-}9$ a class of cyclic molecules containing six or more α-D-glucopyranose units linked at the 1,4 positions by α-linkages as in amylose, and derivatives thereof, were identified in EP 99306411 as particularly useful in the reversal of many of the commonly used neuromuscular blocking agents, or muscle relaxants, such as rocuronium, pancuronium, vecuronium, rapacuronium, mivacurium, atracurium, (cis) atracurium, succinylcholine and tubocurarine.

It has now been found that 6-mercapto-cyclodextrin derivatives having the general formula I Formula I

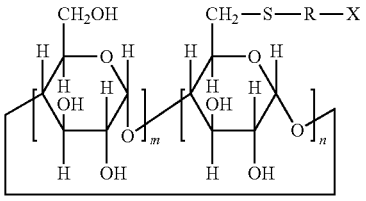

wherein m is 0-7 and n is 1-8 and m+n=7 or 8;

R is $(C_{1-6})$alkylene, optionally substituted with 1-3 OH groups, or $(CH_2)_o$-phenylene-$(CH_2)_p$—;

o and p are independently 0-4;

X is COOH, $CONHR_1$, $NHCOR_2$, $SO_2OH$, $PO(OH)_2$, $O(CH_2—CH_2—O)_q$—H, OH or tetrazol-5-yl;

$R_1$ is H or $(C_{1-3})$alkyl;

$R_2$ is carboxyphenyl;

q is 1-3;

or pharmaceutically acceptable salts thereof;

are highly active in vivo in the reversal of the action of neuromuscular blocking agents.

No protection per se is sought for the following 6-mercapto-cyclodextrin derivatives:

6-per-deoxy-6-per-(2-hydroxyethylthio)-β-cyclodextrin and 6-per-deoxy-6per-(2-hydroxyethylthio)-γ-cyclodextrin, which are described by Ling, C. and Darcy, R. (J. Chem. Soc. Chem Comm. 1993, (2), 203-205);

6-mono-deoxy-6-mono-(2-hydroxyethylthio)-β-cyclodextrin, which is disclosed by Fujita, K. et al. (Tetr. Letters 21, 1541-1544, 1980);

6-per-deoxy-6-per-(carboxymethylthio)-β-cyclodextrin, which is described by Guillo, F. et al. (Bull Chem. Soc. Chim. Fr. 132 (8), 857-866, 1995);

6-mono-deoxy-6-mono-(carboxymethylthio)-β-cyclodextrin, which is described by Akiie, T. et al. (Chem. Lett. 1994 (6), 1089-1092);

6A,6B-dideoxy-6A,6B-bis[(o-carboxyphenyl)thio]-β-cyclodextrin and 6A,6B-dideoxy-6A,6B-bis (carboxymethylthiol)-β-cyclodextrin, which are described by Tubashi, I. et al. (J. Am. Chem. Soc. 108, 4514-4518, 1986; and 6-per-deoxy-6-per-(2,3dihydroxypropylthio)-β-cyclodextrin, which is described by Baer, H. H. and Santoyo-González, F. (Carb. Res. 280, 315-321, 1996). These prior art 6-mercapto-cyclodextrin derivatives have been described in relation with different utilities in each instance.

However, the above mentioned prior art 6-mercapto-cyclodextrin derivatives do belong to the main aspect of the present invention which relates to the use of a 6-mercapto-cyclodextrin derivative according to the general formula I for the manufacture of a medicament for the reversal of drug-induced neuromuscular block.

In one embodiment the invention relates to 6-mercapto-cyclodextrin derivatives having the general formula I, wherein m is 0-7 and n is 1-8 and m+n=7 or 8;

X is COOH, OH or $CONHCH_3$;

R is $(C_{1-6})$alkylene or $(CH_2)_o$-phenylene-$(CH_2)_p$;

o and p are independently 0-4; or a pharmaceutically acceptable salt thereof, with the exclusion of 6-per-deoxy-6-per-(2-hydroxyethylthio)-β-cyclodextrin;

6-mono-deoxy-6-mono-(2-hydroxyethylthio)-β-cyclodextrin;

6-per-deoxy-6-per-(2-hydroxyethylthio)-γ-cyclodextrin;

6-per-deoxy-6-per-(carboxymethylthio)-β-cyclodextrin;

6-mono-deoxy-6-mono-(carboxymethylthio)-β-cyclodextrin;

6A,6B-dideoxy-6A,6B-bis[(o-carboxyphenyl)thio]-β-cyclodextrin; and 6A,6B-dideoxy-6A,6B-bis(carboxymethylthiol)-β-cyclodextrin.

The term $(C_{1-6})$alkylene as used in the definition of formula I means a branched or straight chain bivalent carbon radical containing 1-6 carbon atoms, such as methylene, ethylene (1,2-ethandiyl), propylene (1-methyl-1,2-ethanediyl), 2-methyl-1,2-ethanediyl, 2,2-dimethyl-1,2-ethanediyl, 1,3-propanediyl, 1,4-butanediyl, 1,5-pentanediyl and 1,6-hexanediyl.

The term phenylene means a bivalent moiety the free valencies of which can be positioned either ortho, meta or para to one another.

The term $(C_{1-3})$alkyl means a branched or straight chain alkyl group containing 1-3 carbon atoms, i.e. methyl, ethyl, propyl and isopropyl.

The term carboxyphenyl means a phenyl group which is substituted at either the ortho-, the meta- or the para-position with a carboxy-group. The ortho-carboxyphenyl group is preferred.

Compounds according to formula I wherein n+m is 7 are derivatives of β-cyclodextrin, those wherein n+m is 8 are derived from γ-cyclodextrin.

Preferred are the 6-mercapto-cyclodextrin derivatives of formula I wherein X is COOH, or a pharmaceutically acceptable salt thereof.

More preferred are the 6-mercapto-γ-cyclodextrin derivatives of formula I wherein n is 8, R is $(C_{1-6})$alkylene and X is COOH.

Particularly preferred 6-mercapto-cyclodextrin derivatives of the invention are 6-per-deoxy-6-per-(2-carboxyethyl)thio-γ-cyclodextrin;

6-per-deoxy-6-per-(3-carboxypropyl)thio-γ-cyclodextrin;

6-per-deoxy-6-per-(4-carboxyphenyl)thio-γ-cyclodextrin;

6-per-deoxy-6-per-(4-carboxyphenylmethyl)thio-γ-cyclodextrin;

6-per-deoxy-6-per-(2-carboxypropyl)thio-γ-cyclodextrin; and 6-per-deoxy-6-per-(2-sulfoethyl)thio-γ-cyclodextrin.

The 6-mercapto-cyclodextrin derivatives of formula I can be prepared by reacting a C6-activated cyclodextrin derivative of formula II with an alkylthiol, arylalkylthiol or arylthiol derivative corresponding to H—S—R—X, wherein R and X have the meaning as previously defined, in the presence of an inorganic or organic base.

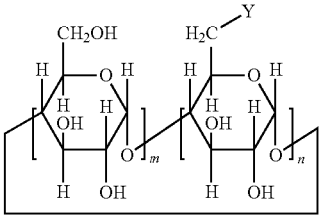

Formula TI wherein m is 0-7, n is 1-8, m+n=7 or 8 and Y is a leaving group which can be a halide (Cl, Br or I), sulfuric ester or a sulfonic ester function, such as a tosylate, a napthtalenesulfonate or a triflate.

Conversely the 6-mercapto-cyclodextrin derivatives of formula I can also be prepared by reacting a 6-thiol γ- or β-cyclodextrin derivative of formula III with an alkylating agent, e.g., alkyl halide, arylalkyl halide, alkyl sulfonate, arylalkyl sulfonate, corresponding to Y—X—R, wherein Y, X and R have the meanings as previously defined, or with a double bond containing reagent, e.g., vinyl alkane, acrylate, etc., or an epoxide in the presence of an inorganic or organic base.

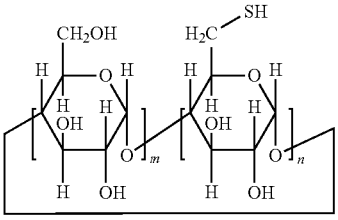

Formula III wherein m is 0-7, n is 1-8, m+n=7 or 8.

Alternative synthesis routes for the preparation of the 6-mercapto-cyclodextrin derivatives of the invention are known to the skilled person. The chemistry of the derivatisation of cyclodextrins is well documented (see for example: Comprehensive Supramolecular Chemistry, Volumes 1-11, Atwood J. L., Davies J. E. D., MacNicol D. D., Vogtle F., eds; Elsevier Science Ltd., Oxford, UK, 1996).

Pharmaceutically acceptable salts of 6-mercapto-cyclodextrin derivatives of formula I wherein X represents the carboxylic acid group COOH, the sulphonic acid group $SO_2OH$, the, phosphonic acid group $PO(OH)_2$ or the tetrazol-5-yl group, may be obtained by treating the acid with an organic base or a mineral base, like sodium-, potassium- or lithium hydroxide.

The 6-mercapto-cyclodextrin derivatives, or pharmaceutically acceptable salts or solvates thereof, for use in the invention are administered parenterally. The injection route can be intravenous, subcutaneous, intradermal, intramuscular, or intra-arterial. The intravenous route is the preferred one. The exact dose to be used will necessarily be dependent upon the needs of the individual subject to whom the medicament is being administered, the degree of muscular activity to be restored and the judgement of the anaesthetist/critical-care specialist. Exfracorporal application of the chemical chelators of the invention, for instance by mixing of the chemical chelator with the blood during dialysis or during plasmapheresis, is also contemplated.

In a further aspect the invention relates to a kit for providing neuromuscular block and its reversal comprising (a) a neuromuscular blocking agent, and (b) a 6mercapto-cyclodextrin derivative according to general formula I capable of forming a guest-host complex with the neuromuscular blocking agent. With a kit according to the invention is meant a formulation, which contains separate pharmaceutical preparations, i.e. the neuromuscular blocking agent and a 6-mercapto-cyclodextrin derivative of formula I, i.e. the reversal agent. The components of such a kit of parts are to be used sequentially, i.e. the neuromuscular blocking agent and a 6-mercapto-cyclodextrin derivative of formula I, i.e. the reversal agent. The components of such a kit of parts are to be used sequentially, i.e. the neuromuscular blocking agent is administered to a subject in need thereof, which is followed, at a point in time when restoration of muscle function is required, by the administration of the reversal agent, i.e. a 6-mercapto-cyclodextrin derivative of the present invention.

A preferred kit, according to the invention, contains a 6-mercapto-cyclodextrin derivative of formula I and a neuromuscular blocking agent which is selected from the group consisting of rocuronium, vecuronium, pancuronium, rapacuronium, mivacurium, atracurium, (cis)atracurium, tubocurarine and suxamethonium. A particularly preferred kit of the invention comprises rocuronium as the neuromuscular blocking agent.

Mixed with pharmaceutically suitable auxiliaries and pharmaceutically suitable liquids, e.g. as described in the standard reference, Gennaro et al., Remington's Pharmaceutical Sciences, (18th ed., Mack Publishing Company, 1990, Part 8: Pharmaceutical Preparations and Their Manufacture; see especially Chapter 84 on "Parenteral preparations", pp. 1545-1569; and Chapter 85 on "Intravenous admixtures", pp. 1570-1580) the 6-mercapto-cyclodextrin derivatives can be applied in the form of a solution, e.g. for use as an injection preparation.

Alternatively, the pharmaceutical composition may be presented in unit-dose or multi-dose containers, for example sealed vials and ampoules, and may be stored in a freeze dried (lyophilised) condition requiring only the addition of the sterile liquid carrier, for example, water prior to use.

The invention further includes a pharmaceutical formulation, as hereinbefore described, in combination with packaging material suitable for said composition, said packaging material including instructions for the use of the composition for the use as hereinbefore described.

The invention is illustrated in the following examples.

EXAMPLE 1

6-mono-Deoxy-6-mono-(4-carboxyphenyl)thio-γ-cyclodextrin, Sodium Salt

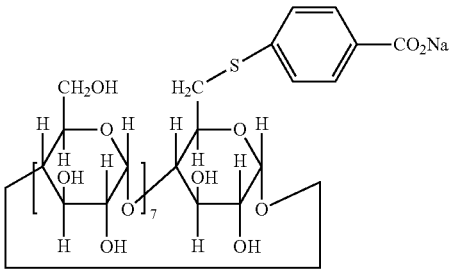

To a round bottom flask containing pyridine (120 ml) was added dry γ-cyclodextrin (2.0 g, 1.54 mmol) under nitrogen at room temperature. After dissolution, 2-napthalenesulfonyl chloride (1.05 g, 4.64 mmol) in pyridine (20 ml) was added and the mixture stirred for 24 h. Quenched with water (50 ml) and evaporated to dryness to leave crude 6-mono-O-(2'-naphthalenesulfonyl)-γ-cyclodextrin.

Sodium hydride (0.38 g, 15.83 mmol) was suspended in dry dimethylformamide (20 ml). 4-Mercaptobenzoic acid (0.7 g, 4.55 mmol) was then added to the suspension and the resulting mixture was stirred for 20 minutes. γ-Cyclodextrin nosylate (3.2 g, 2.12 mmol) was added to the mixture and the reaction was heated to 100° C. for 90 minutes. After cooling, acetone was added to precipitate a solid, which was reprecipitated from water/acetone. This was then dissolved in water (20 ml), pH adjusted to 7.0 by adding 2N hydrochloric acid, then chromatographed on a Sephadex DEAE A-25 column. Appropriate fractions were combined, dialysed, then precipitated, twice from water/acetone to give 400 mg of the titled compound. $^1$H NMR in DMSO δ 7.4 to 7.8 (ArH), 5.0 to 5.2 (8H), 4.13 (1H), 3.7 to 4.0 (29H), 3.7 to 3.4 (17H), 3.25 (1H) ppm. $^{13}$C NMR in DMSO δ 129.9 and 127.5 (ArC), 103.3 and 102.9 (C1 and C1'), 85.0 (C4'), 81.6 (C4), 73.8 (C3), 73.5 (C2), 72.2 (C5), 70.8 (C5'), 60.6 (C6), 34.3 (C6') ppm. Electrospray MS $[M+H]^+$=1455.7 and $[M+Na]^+$ =1477.7.

EXAMPLE 2

6mono-Deoxy-6-mono-(2-carboxyphenyl)thio-γ-cyclodextin, Sodium Salt

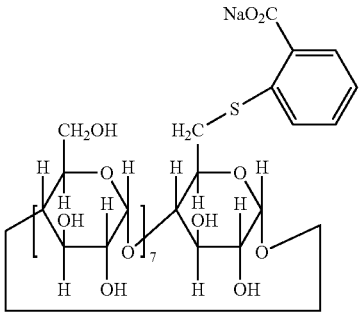

Sodium hydride (60% dispersed in oil, 0.18 g, 4.5 mmol) was added to thiosalicylic acid (0.34 g, 2.2 mmol) in DMF (25 ml) in one portion and stirred at room temperature for 30 min. To this was then added the crude solution of 6-mono-O-(2'-naphthalenesulfonyl)-γ-cyclodextrin (2.5 g, 1.45 mmol) in DMF (15 ml) and heated to 70° C. for 24 h. The mixture was cooled and quenched with water (20 ml) before evaporating to dryness. Water was then added to the residue and the resulting solution was poured into acetone (250 ml) to effect precipitation. The resulting solid was collected by filtration and dissolved in water (10 ml) before passing through a Sephadex DEAE A-25 column eluting with water then 0.2 N NaOH. Fractions containing the product were combined and evaporated to a low volume and dialysed (MWCO 1000) by changing the external water four times. Internal solution was evaporated to low volume and poured into acetone (100 ml). Solid was collected by filtration and dried under vacuum at 70° C. to leave the title compound (235 mg) as a white solid. $^1$H NMR ($D_2O$) δ 7.50-7.10 (4H, m, Ar—H), 5.14 (8H, m, CyD 1-H), 4.16 (1H, m, CyD 5-H), 3.98-3.85 (26H, m, CyD 3,5, 2,4-H), 3.70-3.61 (20H, m, CyD 2,3,4,6-H), 3.15 (1H, m, CyD 6-H) ppm; Electrospray MS m/z 1477.6 for $[M+Na]^+$, calcd for $C_{55}H_{83}NaO_{41}S$ M 1455.304.

EXAMPLE 3

6-Per-deoxy-6-per-(3-carboxyphenyl)thio-γ-cyclodextrin, Sodium Salt

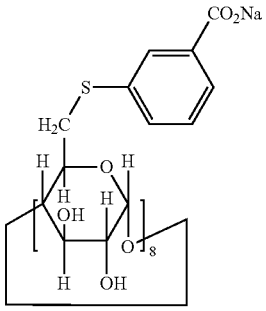

Triphenylphosphine (30.1 g, 15 eq) was dissolved with stirring in dry DMF (160 ml). To this was added iodine (30.5 g, 15.6 eq) over 10 min. with heat evolved. Dry γ-cyclodextrin (10 g, 7.7 mmol) was then added and the mixture was heated to 70° C. for 24 h. The mixture was allowed to cool, to which sodium methoxide (3.1 g sodium in 50 ml methanol) was added and the mixture was stirred for 30 min, before pouring onto methanol (800 ml) and evaporating to dryness. To the residue was added water (500 ml) and the solid was collected by filtration and washed with water (3×100 ml), then acetone (3×100 ml), and dried under vacuum at 70° C. to give 6-per-deoxy-6-per-iodo-γ-cyclodextrin as a yellow solid (16.2 g) which was used without further purification.

To a solution of 3-mercaptobenzoic acid (1.0 g, 10 eq) in DMF (30 ml) was added 60% sodium hydride dispersed in oil (476 mg, 22 eq) portionwise over 30 min. The mixture was cooled and 6-per-deoxy-6-per-iodo-γ-cyclodextrin (1.4 g) in DMF (30 ml) was added. The mixture was then stirred at 70° C. for 24 h. The mixture was allowed to cool to room temperature and quenched with the addition of water (20 ml) before evaporating to a low volume. The solution was poured into acetone (500 ml) and the precipitate was collected by filtration, dissolved in water (20 ml) and dialysed (MWCO 1000) by changing the external water four times. Internal solution was evaporated to low volume and poured into acetone (250 ml). The solid precipitate was collected by filtration and dried under vacuum at 70° C. to afford the title compound (1.45 g) as a white solid: $^1$H NMR ($D_2O$) δ 7.77 (8H, br s, Ar—H), 7.55 (8H, d, J=6.0 Hz, Ar—H), 7.71 (16H, m, Ar—H), 5.16 (8H, s, CyD 1-H), 4.00-3.94 (16H, m, CyD 3,5-H), 3.58-3.53 (16H, m, CyD 4,2-H), 3.43-3.40 (8H, m, CyD 6-H), 3.24-3.20 (8H, m, CyD 6-H); Electrospray m/z 1190.6 for $[M-8Na+6H]^{2-}$, calcd for $C_{104}H_{104}Na_8O_{48}S_8$ M 2562.39.

EXAMPLE 4

6-Per-deoxy-6-per-(2-carboxyethyl)thio-γ-cyclodextrin, Sodium Salt

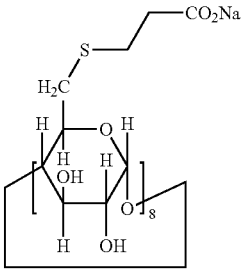

3-Mercaptopropionic acid (1.22 ml, 14.0 mmol) was dissolved in dry DMF (45 ml) under $N_2$ at room temperature. To this solution was added in three portions sodium hydride (1.23 g, 30.8 mmol, 60%) and the mixture was stirred for a further 30 min. To this mixture was then added dropwise a solution of 6-per-deoxy6-per-iodo-γ-cyclodextrin (3.12 g, 1.40 mmol) in 45 ml dry DMF. After addition, the reaction mixture was heated at 70° C. for 12 h. After cooling, water (10 ml) was added to the mixture and the volume was reduced to 40 ml in vacuo, to which ethanol (250 ml) was added resulting in precipitation. The solid precipitate was collected by filtration and dialysed for 36 h. The volume was then reduced to 20 ml in vacuo. To this was added ethanol, and the precipitate was collected by filtration and dried to give the title compound as a white solid (1.3 g, 43%). $^1$H-NMR $D_2O$ δ 2.47-2.51 (m, 16H); 2.84-2.88 (m, 16H); 3.00-3.02 (t, 8H); 3.11-3.14 (t, 8H); 3.62-3.68 (m, 16H); 3.92-3.97 (m, 8H); 4.04-4.06 (m, 8H); 5.19 (m, 8H) ppm. MS FIA +ion at 2024.9 m/z.

EXAMPLE 5

6-Per-deoxy-6-per-(5-carboxypentyl)thio-γ-cyclodextrin, Sodium Salt

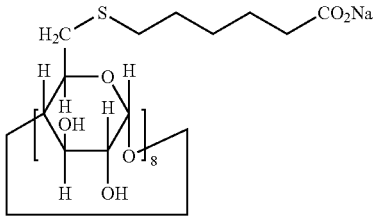

The title compound was prepared in a similar way as described for Example 4 by reacting 6-mercaptohexanoic acid (1.34 g, 0.90 mmol) with 6-per-deoxy-6-per-iodo-γ-cyclodextrin. $^1$H-NMR $D_2O$ δ 1.40 (s, 16H); 1.57-1.64 (m, 32H); 2.17-2.21 (m, 16H); 2.67-3.00 (m, 16H); 2.85-2.90 (m, 8H); 3.15-3.20 (m, 8H); 3.52-3.59 (m, 8H); 3.60-3.63 (m, 8H); 3.87-3.93 (m, 16H); 5.16 (s, 8H) ppm. MS FIA +ions at 2362.2, 2213, 2065 and 1919 m/z.

EXAMPLE 6

6-Per-deoxy-6-per-(3carboxypropyl)thio-γ-cyclodextrin, Sodium Salt

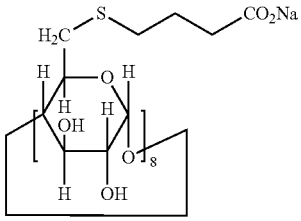

The title compound was prepared in a similar way as described for Example 4 by reacting 4-mercaptobutyric acid (1.10 g, 0.009 mol) with 6-per-deoxy-6-per-iodo-γ-cyclodextrin. $^1$H-NMR $D_2O$ δ 1.87-1.88 (m, 16H); 2.27-2.30 (m, 16H); 2.67-2.71 (m, 16H); 2.98-3.00 (m, 8H); 3.13-3.16 (m, 8H); 3.61-3.63 (m, 16H); 3.94-4.03 (m, 16H); 5.21 (s, 8H) ppm. MS FIA +ion at 2138.8 m/z.

EXAMPLE 7

6-Per-deoxy-6-per-carboxymethylthio-γ-cyclodextrin, Sodium Salt

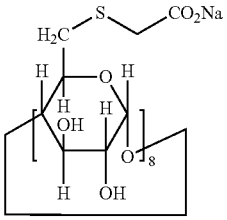

Sodium hydride (60% dispersion, 0.34 g, 8.60 mmol) was added to a stirred solution of ethyl 2-mercaptoacetate (0.92 ml, 8.40 mmol) in DMF (20 ml) under nitrogen at room temperature. After effervescence had ceased (15 min), per-6-deoxy-per-6-iodo-γ-cyclodextrin (2.17 g, 1.00 mmol) was added to the system. After a further 5 min, the temperature was raised to 70° C. and the reaction was left with stirring for 17 h. After cooling, DMF was removed in vacuo. Methanol (50 ml) was added and a creamy white solid slowly crystallised out of solution. This was filtered off under suction, washed with methanol and dried to give 6-per-deoxy-6-per-carbethoxymethylthio-γ-cyclodextrin as a solid (1.74 g, 82%). $\delta_H$ (d6-dmso) 4.95-4.85 (8H, m, 8×anomeric CH), 4.05 (16H, q, 8×$CH_2CH_3$), 3.85-3.75 (8H, m), 3.60-3.50 (8H, m), 3.40-3.20 (32H, bs, 8×$CH_2SCH_2$), 3.20-3.10 (8H, m), 2.95-2.85 (8H, m), 1.20 (24H, t, 8×$CH_2CH_3$).

To 1 M solution of sodium hydroxide (7 ml) was added 6-per-deoxy-6-per-carbethoxymethylthio-γ-cyclodextrin (1.00 g, 0.47 mmol) and the reaction was allowed to stir at room temperature. After 18 h, the clear solution was dialysed for 8 h, with water (2 L) being replaced every 2 h. After this time, the contents of the dialysis tubing was emptied into a flask and water evaporated in vacuo, giving the title compound as a white solid (0.62 g, 64%). $\delta_H$ ($D_2O$) 5.21 (8H, d, 8×anomeric CH), 4.18-4.05 (8H, m), 4.00 (8H, dd), 3.78 (8H, dd), 3.70 (8H, $\overline{d}$d), 3.40 (16H, dd), 3.20 (8H, d), 3.02 (8H, dd). $\delta_C$ ($D_2O$) 178.1, 101.6, 82.8, 73.0, 72.7, 71.8, 39.0, 34.1 LC/MS TOF 1889 m/z.

EXAMPLE 8

6-Per-deoxy-6-per-(4-carboxyphenyl)thio-γ-cyclodextrin, Sodium Salt

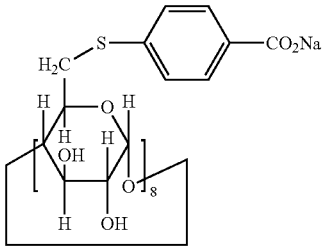

To a solution of 4-mercaptobenzoic acid (856 mg) in DMF (30 ml) was added 60% sodium hydride dispersed in oil (372 mg) portionwise over 30 min. The mixture was cooled and per-6-deoxy-per-6-bromo-γ-cyclodextrin (1.0 g) was added in one portion and the mixture was stirred at 70° C. for 24 h. The mixture was allowed to cool to room temperature and quenched with the addition of water (20 ml) before evaporating to a low volume. The solution was poured into ethanol (250 ml) and the precipitate was collected by filtration, dissolved in water (20 ml) and dialysed (MWCO 1000) by changing the external water four times. Internal solution was evaporated to low volume and poured into acetone (250 ml). The solid precipitate was collected by filtration and dried under vacuum at 70° C. to afford the title compound (1.2 g) as a white solid. $^1$H NMR ($D_2O$, 343K) δ 7.70 (16H, d, J=8.1 Hz, Ar—H), 7.23 (16H, d, J=7.3 Hz, Ar—H), 5.15 (8H, s, CyD 1-H), 4.00-3.96 (16H, m, CyD 3,5-H), 3.55-3.53 (24H, m, CyD 6',4,2-H), 3.15 (8H, m, CyD 6-H); MALDI-TOF m/z 2383.7 for [M−$Na_8$+$H_6$], calcd for $C_{104}H_{104}Na_8O_{48}S_8$ M 2562.39.

EXAMPLE 9

6-Per-deoxy-6-per-(4-carboxymethylphenyl)thio-γ-cyclodextrin, Sodium Salt

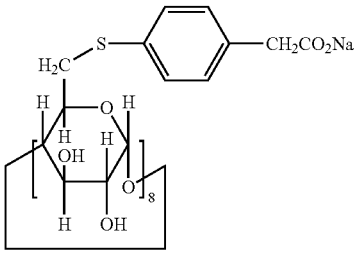

To a solution of 4-mercaptophenylacetic acid (10 eq) in DMF (50 ml) was added 60% sodium hydride in oil (22 eq) portionwise over 30 min. The mixture was cooled and per-6-deoxy-per-6-bromo-γ-cyclodextrin (1.0 g) was added in one portion and the mixture was stirred at 70° C. for 24 h. The mixture was allowed to cool to room temperature and quenched with the addition of water (20 ml) before evaporating to a low volume. The solution was then poured into acetone (250 ml) and the precipitate was collected by filtration, suspended in water (20 ml) and dialysed (MWCO 1000) by changing the external water four times. Internal solution was evaporated to low volume and poured into acetone (250 ml). The solid precipitate was collected by filtration and dried under vacuum at 70° C. to afford the title compound (1.44 g) as a white solid. $^1$HNMR ($D_2O$, 343K) δ 7.15 (16H, d, J=8.0 Hz, Ar—H), 6.99 (16H, d, J=8.0 Hz, Ar—H), 4.98 (8H, s, CyD 1-H), 3.90-3.72 (16H, m, CyD 3,5-H), 3.51-3.43 (16H, m, CyD 4,2-H), 3.28 (24H, m, $CH_2$—Ar, CyD 6'-H), 3.15-3.10 (1H, m, CyD 6-H); MALDI-TOF m/z 2495.8 for [M−$Na_8$+$H_6$], calcd for $C_{112}H_{120}Na_8O_{48}S_8$ M 2674.6.

EXAMPLE 10

6-Per-deoxy-6-per(3-amidopropyl)thio-γ-cyclodextrin

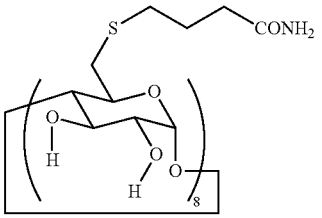

To a mixture of 6-per-deoxy-6-per-thio-γ-cyclodextrin (500 mg; prepared as described in Example 17) and potassium iodide (5 mg) in DMF (10 ml) was added 4-chlorobutamide (673 mg; Fries et. al. Biochemistry 1975, 14, 5233). Caesium carbonate (1.8 g) was added and the reaction mixture was heated to 60° C. overnight. The resulting mixture was poured into acetone, filtered, washed with ethanol and water and then dried in-vacuo (118 mg; 16.2%). $^1$H NMR (DMSO/$D_2O$) δ 4.9 (1H, s), 3.8 (1H, m), 3.6 (1H, m), 3.4 (2H, m), 3.05 (1H, m), 2.85 (1H, m), 2.2 (2H, m), 1.75 (2H, m). Electrospray Mass Spectrum M−H (m/z) 2105.

EXAMPLE 11

6-Per-deoxy-6-per(5-hydroxy-3-oxa-pentyl)thio-γ-cyclodextrin

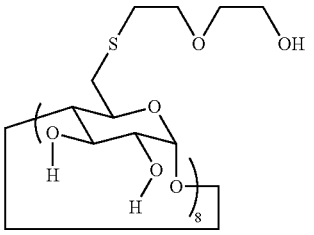

2-(2-Mercaptoethoxy)ethanol (1.4 g, 11.6 mmol) was dissolved in DMF (20 ml) and stirring commenced at room temperature under a nitrogen atmosphere. Per-6-bromo-γ-cyclodextrin (2 g, 1.12 mmol) and caesium carbonate (3.2 g, 9.86 mmol) were then added and the resultant suspension stirred at 60° C. overnight under a nitrogen atmosphere. After cooling to room temperature the suspension was poured into acetone (200 ml) and the insoluble material isolated by filtration, washed with acetone (×3) and dried in vacuo. The crude product was dissolved in de-ionised water (20 ml) and dialysed (10 h). The contents of the dialysis membrane were then concentrated in vacuo to yield 1 g of the desired product as a cream solid.

$^1$H NMR ($D_2O$, 400 MHz): δ 2.81-3.00 (m, 24H), 3.21-3.31 (d, 8H), 3.49 (t, 8H), 3.55-3.75 (m, 56H), 3.82 (t, 8H), 3.89 (t, 8H), 5.11 (d, 8H). ESI-MS: 2175 $(M-H)^-$.

EXAMPLE 12

6-Per-deoxy-6-per[(2(2-carboxybenzoyl)amino) ethyl]thio-γ-cyclodextrin, Sodium Salt

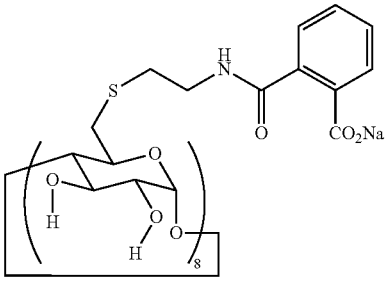

Per-6-mercapto-γ-cyclodextrin (1 g, 0.7 mmol; see example 17) was dissolved in DMF (10 ml) and stirring commenced at room temperature under a nitrogen atmosphere. N-(2-Bromoethyl)phthalimide (1.57 g, 6.17 mmol) and caesium carbonate (2 g, 6.17 mmol) were added and the resultant suspension was stirred at 60° C. overnight under a nitrogen atmosphere. After cooling to room temperature the DMF was removed in vacuo and water (100 ml) was added with vigorous stirring. The precipitate was isolated by filtration, washed with water (×3) and dried in vacuo to yield 1.67 g of a cream solid. Aqueous sodium hydroxide (1M, 20 ml) was then added to the crude product (600 mg) and the resultant solution stirred at room temperature overnight under a nitrogen atmosphere. The solution was then dialysed with de-ionised water until constant pH and the contents of the dialysis membrane dried in vacuo to yield 500 mg of the desired product as a glassy solid. $^1$H NMR ($D_2O$, 400 MHz): δ 2.76-2.96 (m, 24H), 3.10-3.30 (m, 8H), 3.35-3.62 (m, 32H), 3.78-3.95 (m, 16H), 5.02 (d, 8H), 7.30-7.62 (m, 32H); ESI-MS: 1477 $(M-2H)^{2-}$.

EXAMPLE 13

6-Per-deoxy-6-per(2-hydroxyethyl)thio-γ-cyclodextrin

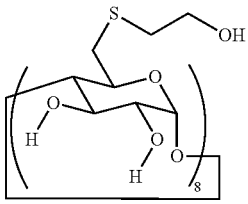

To a stirred solution of 2-mercaptoethanol (10.85 g, 10 eq) in DMF (500 ml) under nitrogen was added 60% sodium hydride dispersed in oil (11.7 g, 21 eq) portion-wise over 30 min. The mixture was stirred at room temperature for 90 minutes. Per-6-deoxy-6-per-bromo-γ-cyclodextrin (25.0 g) was added and the mixture heated to 70° C. for 24 h. The mixture was allowed to cool to room temperature and quenched by addition of water (50 ml) before evaporating to a low volume. The residue was taken up in water (100 ml) and poured onto 1:1 methanol/acetone (500 ml). The solid formed was collected by filtration, dissolved in water (500 ml) and dialysed (MWCO 1000) changing the external water four times. The internal solution was evaporated to low volume and then re-crystallised from hot water to afford the title compound (8.5 g) as white cross-shaped crystals.

$^1$H NMR (400 MHz; DMSO) δ 5.91 (16H, br s, 2,3-OH), 4.92 (8H, s, 1-H), 4.71 (8H, t, J 4.4 Hz, $SCH_2CH_2OH$), 3.75 [8H, t, J 8.0 Hz, 3-H (or 5-H)], 3.60-3.50 [24H, m, 5-H (or 3-H), $SCH_2CH_2OH$], 3.40-3.30 (16H, m, 4-H, 2-H), 3.08 (8H, d, J 13.6 Hz, 6-H), 2.82 (8H, dd, J 13.6, 6.8 Hz, 6-H), 2.66 (16H, t, J 6.8 Hz, $SCH_2CH_2OH$); m/z (electrospray) 1775.4 for $[M-H]^-$, calcd for $C_{64}H_{112}S_8O_{40}$ M 1776.45.

The preparation of this compound by a similar method has been published previously: J. Chem. Soc., Chem. Commun., 203 (1993).

EXAMPLE 14

6-Per-deoxy-6-per(N-methylamidomethyl)thio-γ-cyclodextrin

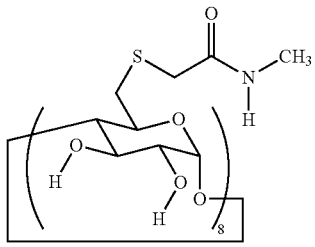

To a stirred solution of N-methyimercaptoacetamide (0.58 g, 10 eq) in DMF (30 ml) under nitrogen was added 60% sodium hydride dispersed in oil (0.22 g, 10 eq) portion-wise over 30 min. The mixture was stirred at room temperature for 30 minutes. Per-6-deoxy-6-per-bromo-γ-cyclodextrin (1.0 g) was added and the mixture heated to 60-70° C. for 48 h. The mixture was allowed to cool to room temperature and quenched by addition of water (20 ml) before evaporating to a low volume. The residual solution was poured onto ethanol (100 ml). The solid formed was collected by filtration, dissolved in water (200 ml) and dialysed (MWCO 1000), changing the external water four times. The internal solution was evaporated to low volume and poured onto ethanol (100 ml). The precipitate was collected by filtration and dried under vacuum to afford the title compound (0.55 g) as a white solid.

$^1$H NMR (400 MHz; $D_2O$) δ 5.29 (8H, d, J 4.0 Hz, 1-H), 4.10 (8H, br t, J 9.6 Hz, 5-H), 4.05 (8H, t, J 9.8 Hz, 3-H), 3.83 (8H, dd, J 10.0, 3.6 Hz, 2-H), 3.74 (8H, t, J 9.2 Hz, 4-H), 3.58-3.49 [16H, AB system, $SCH_2C(O)NHCH_3$], 3.36 (8H, br d, J 12.8 Hz, 6-H), 3.07 (8H, dd, J 14.0, 8.4 Hz, 6-H), 2.94

(24H, s, $SCH_2C(O)NHCH_3$); m/z (electrospray) 1991.7 for $[M-H]^-$, calculated for $C_{72}H_{120}N_8S_8O_{40}$ M 1992.54.

EXAMPLE 15

6-Per-deoxy-6-per(2-carboxypropyl)thio-γ-cyclodextrin, Sodium Salt

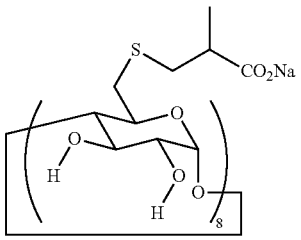

Sodium hydride (60% in oil) (0.44 g) was added to methyl 3-mercapto-2-methyl-propionate (1.474 g; J. Med. Chem., 1994, 1159) in dimethylformamide (25 ml). After 30 minutes per-6-deoxy-per-6-bromo-γ-cyclodextrin (2.25 g), dissolved in dimethylformamide (25 ml), was added. A crystal of sodium iodide was added and the mixture heated at 75° C. overnight. The solvent was distilled off and the residue crystallised from methanol to give the methyl ester (1.3 g). Mass spec. (M−H) 2224;

$^1$H NMR (dmso $D_6$): δ 1.41 (d, 24H), 2.68 (m, 16H), 2.80 (m, 16H), 3.00 (m, 8H), 3.61 (3, 24H), 3.79 (m, 8H), 4.95 (s, 8H).

This product was then stirred overnight with sodium hydroxide solution (M, 13 ml). The resulting mixture was filtered, dialysed to neutrality, and evaporated to dryness to give the title compound (1.13 g). Mass spec. (M−H) 2112; $^1$H NMR (D2O): δ 1.15 (d, 24H), 2.5 (m, 8H), 2.65 (m, 8H), 2.8-3.1 (m, 24H), 3.65 (16H), 4.0 (m, 16H), 5.2 (s, 8H).

EXAMPLE 16

6-Per-deoxy-6-per(3-carboxypropyl)thio-β-cyclodextrin, Sodium Salt

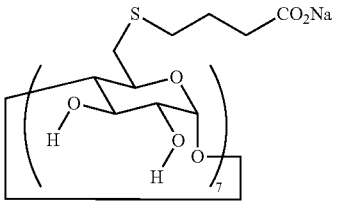

Per-6-deoxy-per-6-bromo-β-cyclodextrin (2.25 g), methyl-4-mercaptobutyrate (1.7 g; Tetrahedron 1998, 2652), cesium carbonate (4.24 g) and dimethylformamide (25 ml) were stirred and heated together for three days. The mixture was cooled, poured into water and filtered. The solid was washed with methanol and dried (2.1 g). This was stirred overnight with sodium hydroxide solution (M, 21 ml), filtered and the filtrate dialysed to neutrality. This was evaporated to dryness giving the title compound (1.7 g). Mass Spec. (M−H) 1848.8. $^1$H NMR ($D_2O$): δ 1.75 (m, 16H), 2.15 (m, 16H), 2.6 (m, 16H), 2.85 (m, 8H), 3.05 (m, 8H), 3.55 (m, 16H) 3.87 (m, 16H), 5.07 (s, 8H).

EXAMPLE 17

6-Per-deoxy-6-per(2-sulfoethyl)thio-γ-cyclodextrin, Sodium Salt

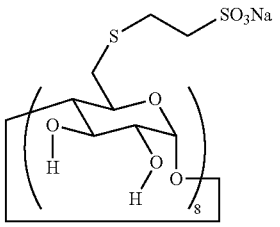

A: Per-6-deoxy-per-6-thio-γ-cyclodextrin

Per-6-deoxy-per-6-bromo-γ-cyclodextrin (20 g), thiourea (13.5 g) and dimethylformamide (100 ml) were heated together for three days at 65° C. and then ethanolamine (20 ml) was added and heating continued for two hours. The mixture was cooled, diluted with ice water and the product separated by centrifuge. The solid was washed twice with water and dried in vacuum at 65° C. giving the thiol (7.34 g).

Mass spec. (M−H) 1424. $^1$H NMR (dmso $D_6$): δ 2.82 (m, 8H), 3.20 (d, 8H), 3.35 (m, 16H), 6.65 (t, 8H), 7.75 (t, 8H), 5.0 (s, 8H).

B: 6-Per-deoxy-6-per(2-sulfoethyl)thio-γ-cyclodextrin, Sodium Salt

The above per-thiol (1 g), 2-bromoethane sulphonic acid sodium salt (1.42 g), cesium carbonate (2.2 g) and dimethylformamide (10 ml) were stirred and heated overnight at 64° C. Most of the solvent was evaporated under vacuum and the residue dissolved in water. Sodium bicarbonate solution (5% w/w, 5 ml) was added and the solution dialysed three times with water. This solution was evaporated to dryness and the residue dissolved in sodium bicarbonate solution (10 ml), dialysed and evaporated as before. This process was repeated, the resulting solid was dissolved in a small volume of water and the product precipitated with methanol. This was dissolved in water and evaporated to dryness giving the title compound (1.18 g).

$^1$H NMR ($D_2O$): δ 3.9 (m, 24H), 3.2 (m, 24H), 3.55-3.65 (m, 16H), 3.9 (m, 8H), 4.05 (m, 8H), 5.15 (s, 8H).

EXAMPLE 18

6-Per-deoxy-6-per(2,2-di(hydroxymethyl)-3-hydroxy-propyl)thio-γ-cyclodextin

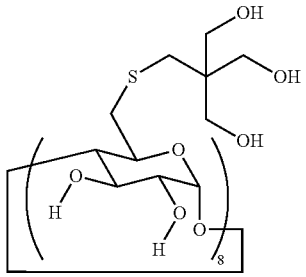

Per-6-deoxy-per-6-thio-γ-cyclodextrin (500 mg; Example 17), 3-bromo-2,2-dihydroxy-methylpropanol (670 mg), cesium carbonate (550 mg) and dimethyiformamide (10 ml) were heated and stirred for 35 days at 65° C. until analysis by LCMS showed conversion to the required product. The mixture was evaporated to dryness, dissolved in water, dialysed against water, evaporated to low, volume and precipitated with acetone. Drying under vacuum gave the title compound (550 mg).

Mass spec. FIA (M−H) 2369. $^1$H NMR ($D_2O$): δ 2.84 (m, 16H), 3.15 (m, 8H), 3.24 (m, 8H), 3.69 (s, 64H), 3.85-4.19 (m, 16H), 5.25 (s, 8H).

EXAMPLE 19

6-Per-deoxy-6-per(3-(tetrazol-5-yl)propyl)thio-γ-cyclodextrin, Sodium Salt

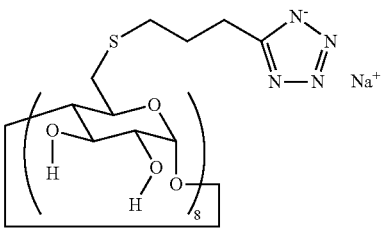

Per-6-deoxy-per-6-thio-γ-cyclodextrin (1 g), 4-bromobutyronitrile (1 g), cesium carbonate (1 g) and dimethylformamide (10 ml) were stirred together at 60° C. over the weekend. The mixture was cooled, water added and the precipitate separated by centrifuge. After washing and drying the perbutyronitrile (1.4 g) was obtained. This product (1 g), sodium azide (1.3 g), triethylamine hydrochloride (2.8 g) and dimethylformamide (13 ml) were stirred and heated together for 7 days at 100° C. The mixture was cooled, diluted with water, acidified and the precipitated filtered off. This was washed with water, sonicated with methanol, separated by centrifuge, dried and dissolved in sodium hydroxide solution (M, 10 ml), filtered and dialysed to neutrality. This solution was evaporated to dryness to give the title compound (600 mg). Mass spec. (M−2H) 1152.8.

$^1$H NMR ($D_2O$); δ 1.95 (m, 16H), 2.55 (m, 16H), 2.85 (m, 24H), 3.05 (d, 8H), 3.5 (m, 8H), 3.6 (m, 8H), 3.9 (m, 16H), 5.06 (s, 8H).

EXAMPLE 20

Reversal of Neuromuscular Blockade in Anaesthetized Guinea Pigs in vivo

Male Dunkin-Hartley guinea pigs (bodyweight: 600-900 g) were anaesthetized by i.p. administration of 10 mg/kg pentobarbitone and 1000 mg/kg urethane. After tracheotomy, the animals were artificially ventilated using a Harvard small animal ventilator. A catheter was placed into the carotid artery for continuous monitoring of arterial blood pressure and the taking of blood samples for blood gas analysis. Heart rate was derived from the blood pressure signal. The sciatic nerve was stimulated (rectangular pulses of 0.5 ms duration at 10 s (0.1 Hz) intervals at a supramaximal voltage, using a Grass S88 Stimulator) and the force of M. gastrocnemius contractions was measured using a Grass FT03 force-displacement transducer. Contractions, blood pressure and heart rate were recorded on a multichannel Grass 7D recorder. Catheters were placed in both jugular veins. One catheter was used for the continuous infusion of a neuromuscular blocking agent. The infusion rate of the neuromuscular blocking agent was increased until a steady-state block of 85-90% was obtained. The other catheter was used for administration of increasing doses of the reversal agent. During continuous infusion of the neuromuscular blocking agent, single doses of increasing concentration of reversal agent were given. At the end of the experiment, the measured force of muscle contractions was plotted against the concentration of reversal agent, and using regression analysis techniques, the 50% reversal concentration was calculated. Results for the reversal of the neuromuscular block, induced by the muscle relaxant rocuronium bromide (Roc), by the 6-mercapto-cyclodextrin derivatives of Examples 1-19 are presented in Table I. For comparison, the reversal activity of the parent compounds β-cyclodextrin and γ-cyclodextrin are included as well.

TABLE 1

Dose ($ED_{50}$, μmol · kg$^{-1}$) producing 50% reversal of steady-state neuromuscular block in anaesthetized guinea pigs and concentration at mamimum reversal.

| Compound | $ED_{50}$ μmol · kg$^{-1}$ | % max reversal at conc. (μmol · kg$^{-1}$) |
|---|---|---|
| γ-cyclodextrin (γ-CD) | 4 | 104 (47) |
| β-cyclodextrin (β-CD) | 20 | 93 (113) |
| 6-mono-deoxy-6-mono-(4-carboxyphenyl)-thio-γ-cyclodextrin, Na salt (example 1) | 0.94 | 102 (8.0) |
| 6-mono-deoxy-6-mono-(2-carboxyphenyl)-thio-γ-cyclodextrin (example 2) | 1.30 | 93 (11) |
| 6-per-deoxy-6-per-(3-carboxyphenyl)thio-γ-cyclodextrin (example 3) | 0.28 | 102 (1.28) |
| 6-per-deoxy-6-per-(2-carboxyethyl)thio-γ-cyclodextrin, Na salt (example 4) | 0.09 | 97 (0.53) |
| 6-per-deoxy-6-per-(5-carboxypentyl)thio-γ-cyclodextrin, Na salt (example 5) | 0.74 | 78 (2.5) |
| 6-per-deoxy-6-per-(3-carboxypropyl)thio-γ-cyclodextrin, Na salt (example 6) | 0.09 | 108 (0.48) |
| 6-per-deoxy-6-per-carboxymethylthio-γ-cyclodextrin, Na salt (example 7) | 0.21 | 88 (1.92) |
| 6-per-deoxy-6-per-(4-carboxyphenyl)thio-γ-cyclodextrin, Na salt (example 8) | 0.10 | 95 (0.48) |
| 6-per-deoxy-6-per-(4-carboxyphenylmethyl)-thio-γ-cyclodextrin, Na salt (example 9) | 0.13 | 100 (0.50) |
| 6-per-deoxy-6-per-(3-amidopropyl)thio-γ-cyclodextrin (example 10) | 0.57 | 94 (33) |
| 6-per-deoxy-6-per-(5-hydroxy-3-oxa-pentyl)-thio-γ-cyclodextrin (example 11) | 0.47 | 92 (2.1) |
| 6-per deoxy-6-per-[(2(2 carboxybenzoyl)-amino)ethyl]-thio-γ-cyclodextrin, sodium salt (example 12) | 0.085 | 95 (0.48) |
| 6-per-deoxy-6-per-(2-hydroxyethyl)thio-γ-cyclodextrin (example 13) | 0.20 | 96 (2.0) |
| 6-per-deoxy-6-per-(N-methylamidomethyl)-thio-γ-cyclodextrin (example 14) | 1.54 | 102 (7.3) |
| 6-per-deoxy-6-per-(2-carboxypropyl)thio-γ-cyclodextrin, sodium salt. (example 15) | 0.10 | 103 (0.48) |
| 6-per-deoxy-6-per-(3-carboxypropyl)thio-β-cyclodextrin, sodium salt (example 16) | 0.5 | 100 (3.2) |
| 6-per-deoxy-6-per-(2-sulfoethyl)thio-γ-cyclodextrin, sodium salt (example 17) | 0.055 | 106 (1.7) |
| 6-per-deoxy-6-per-(2,2,di(hydroxymethyl)-3-hydroxy-propyl)thio-γ-cyclodextrin (example 18) | 2.9 | 63 (4.9) |
| 6-per-deoxy-6-per-(3-(tetrazol-5-yl)-propyl)thio-γ-cyclodextrin, sodium salt (example 19) | 0.22 | 109 (1.2) |

What is claimed is:

1. A 6-mercapto-cyclodextrin derivative having the general formula I

Formula I

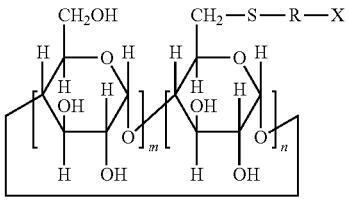

wherein m is 0-7 and n is 1-8 and m+n=7 or 8;

R is $(C_{1-6})$alkylene, optionally substituted with 1-3 OH groups, or $(CH_2)_o$-phenylene-$(CH_2)_p$;

o and p are independently 0-4;

X is COOH, $CONHR_1$, $NHCOR_2$, $SO_2OH$, $PO(OH)_2$, $O(CH_2—CH_2—O)_q—H$, OH or tetrazol-5-yl;

$R_1$ is H or $(C_{1-3})$alkyl;

$R_2$ is carboxyphenyl;

q is 1-3;

or pharmaceutically acceptable salts thereof; with the exclusion of 6-per-deoxy-6-per-(2-hydroxyethylthio)-β-cyclodextrin;

6-mono-deoxy-6-mono-(2-hydroxyethylthio)-β-cyclodextrin;

6-per-deoxy-6-per-(2-hydroxyethylthio)-γ-cyclodextrin;

6-per-deoxy-6-per-(carboxymethylthio)-β-cyclodextrin;

6-mono-deoxy-6-mono-(carboxymethylthio)-β-cyclodextrin;

6A,6B-dideoxy-6A,6B-bis((o-carboxyphenyl)thio)-β-cyclodextrin;

6A,6B-dideoxy-6A,6B-bis(carboxymethylthiol)-β-cyclodextrin and 6-per-deoxy-6-per-(2,3-dihydroxypropylthio)-β-cyclodextrin.

2. The 6-mercapto-cyclodextrin derivative according to claim 1, wherein R, m and n are defined as in claim 1 and X is COOH or $SO_2OH$; or a pharmaceutically acceptable salt thereof.

3. The 6-mercapto-cyclodextrin derivative according to claim 1, wherein m is 0; n is 8; R is $(C_{1-6})$alkylene or $(CH_2)_o$-phenylene-$(CH_2)_p$; o and p are independently 0-4; and X is COOH or $SO_2OH$; or a pharmaceutically acceptable salt thereof.

4. A 6-mercapto-cyclodextrin derivative according to claim 1 selected from the group consisting of:

6-per-deoxy-6-per-(2-carboxyethyl)thio-γ-cyclodextrin;

6-per-deoxy-6-per-(3-carboxypropyl)thio-γ-cyclodextrin;

6-per-deoxy-6-per-(4-carboxyphenyl)thio-γ-cyclodextrin;

6-per-deoxy-6-per-(4-carboxyphenylmethyl)thio-γ-cyclodextrin;

6-per-deoxy-6-per-(2-carboxypropyl)thio-γ-cyclodextrin; and 6-per-deoxy-6-per-(2-sulfoethyl)thio-γ-cyclodextrin;

or a pharmaceutically acceptable salt thereof.

5. A pharmaceutical composition comprising a 6-mercapto-cyclodextrin derivative having the general formula I Formula I

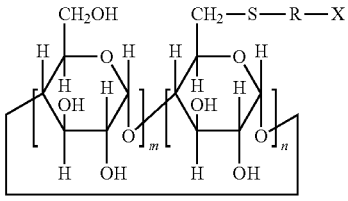

wherein m is 0-7 and n is 1-8 and m+n=7 or 8;

R is $(C_{1-6})$alkylene, optionally substituted with 1-3 OH groups, or $(CH_2)_o$-phenylene-$(CH_2)_p$;

o and p are independently 0-4;

X is COOH, $CONHR_1$, $NHCOR_2$, $SO_2OH$, $PO(OH)_2$, $O(CH_2—CH_2—O)_q—H$, OH or tetrazol-5-yl;

$R_1$ is H or $(C_{1-3})$alkyl;

$R_2$ is carboxyphenyl;

q is 1-3;

or a pharmaceutically acceptable salt thereof, with the exclusion of 6-per-deoxy-6-per-(2-hydroxyethylthio)-β-cyclodextrin;

6-mono-deoxy-6-mono-(2-hydroxyethylthio)-β-cyclodextrin;

6-per-deoxy-6-per-(2-hydroxyethylthio)-γ-cyclodextrin;

6-per-deoxy-6-per-(carboxymethylthio)-β-cyclodextrin;

6-mono-deoxy-6-mono-(carboxymethylthio)-β-cyclodextrin;

6A,6B-dideoxy-6A,6B-bis((o-carboxyphenyl)thio)-β-cyclodextrin;

6A,6B-dideoxy-6A,6B-bis(carboxymethylthiol)-β-cyclodextrin and 6-per-deoxy-6-per-(2,3-dihydroxypropylthio)-β-cyclodextrin, in admixture with pharmaceutically acceptable auxilliaries.

6. A kit for providing neuromuscular block and its reversal comprising (a) a neuromuscular blocking agent, and (b) a 6-mercapto-cyclodextrin derivative according to the general formula I Formula I

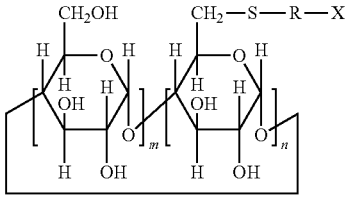

wherein m is 0-7 and n is 1-8 and m+n=7 or 8;

R is $(C_{1-6})$alkylene, optionally substituted with 1-3 OH groups, or $(CH_2)_o$-phenylene-$(CH_2)_p$;

o and p are independently 0-4;

X is COOH, $CONHR_1$, $NHCOR_2$, $SO_2OH$, $PO(OH)_2$, $O(CH_2—CH_2—O)_q—H$, OH or tetrazol-5-yl;

$R_1$ is H or $(C_{1-3})$alkyl;

$R_2$ is carboxyphenyl;

q is 1-3;

or a pharmaceutically acceptable salt thereof.

7. The kit according to claim 6, wherein the neuromuscular blocking agent is selected from the group consisting of rocuronium, vecuronium, pancuronium, rapacuronium, mivacurium, (cis)atracurium, tubocurarine and suxamethonium.

8. The kit according to claim 6, wherein the neuromuscular blocking agent is rocuronium.

9. A method for reversal of drug-induced neuromuscular block in a patient, which comprises parenterally administering to said patient an effective amount of a 6-mercaptocyclodextrin derivative according to the general formula I Formula I

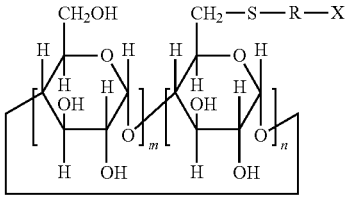

wherein m is 0-7 and n is 1-8 and m+n=7 or 8;

R is $(C_{1-6})$alkylene, optionally substituted with 1-3 OH groups, or $(CH_2)_o$-phenylene-$(CH_2)_p$;

o and p are independently 0-4;

X is COOH, $CONHR_1$, $NHCOR_2$, $SO_2OH$, $PO(OH)_2$, $O(CH_2—CH_2—O)_q$—H, OH or tetrazol-5-yl;

$R_1$ is H or $(C_{1-3})$alkyl;

$R_2$ is carboxyphenyl;

q is 1-3;

or a pharmaceutically acceptable salt thereof.

*10. The kit according to claim 6, wherein the neuromuscular blocking agent is vecuronium.*

*11. 6-Per-deoxy-6-per-(2-carboxyethyl)thio-γ-cyclodextrin, or a pharmaceutically acceptable salt thereof.*

*12. 6-Per-deoxy-6-per-(2-carboxyethyl)thio-γ-cyclodextrin, sodium salt.*

*13. A pharmaceutical composition comprising 6-per-deoxy-6-per-(2-carboxyethyl)thio-γ-cyclodextrin, or a pharmaceutically acceptable salt thereof, and a pharmaceutically suitable auxiliary.*

*14. A pharmaceutical composition comprising 6-per-deoxy-6-per-(2-carboxyethyl)thio-γ-cyclodextrin, sodium salt, and a pharmaceutically suitable auxiliary.*

*15. A kit for providing neuromuscular block and its reversal comprising (a) a neuromuscular blocking agent, and (b) 6-per-deoxy-6-per-(2-carboxyethyl)thio-γ-cyclodextrin, or a pharmaceutically acceptable salt thereof.*

*16. A kit for providing neuromuscular block and its reversal comprising (a) a neuromuscular blocking agent, and (b) 6-per-deoxy-6-per-(2-carboxyethyl)thio-γ-cyclodextrin, sodium salt.*

*17. The kit according to claim 15, wherein the neuromuscular blocking agent is selected from the group consisting of rocuronium, vecuronium, pancuronium, rapacuronium, mivacurium, (cis)atracurium, tubocurarine and suxamethonium.*

*18. The kit according to claim 15, wherein the neuromuscular blocking agent is rocuronium.*

*19. The kit according to claim 15, wherein the neuromuscular blocking agent is vecuronium.*

*20. A method for reversal of drug-induced neuromuscular block in a subject, which comprises parenterally administering to said subject an effective amount of 6-per-deoxy-6-per-(2-carboxyethyl)thio-γ-cyclodextrin, or a pharmaceutically acceptable salt thereof.*

*21. A method for reversal of drug-induced neuromuscular block in a subject, which comprises parenterally administering to said subject an effective amount of 6-per-deoxy-6-per-(2-carboxyethyl)thio-γ-cyclodextrin, sodium salt.*

* * * * *